United States Patent [19]
Shimizu et al.

[11] Patent Number: 5,403,261
[45] Date of Patent: Apr. 4, 1995

[54] ILLUMINATION EQUIPMENT

[75] Inventors: Masanori Shimizu; Syouetu Sakamoto, both of Osaka, Japan

[73] Assignee: Matsushita Electric Industrial Co., Ltd., Japan

[21] Appl. No.: 58,160

[22] Filed: May 5, 1993

Related U.S. Application Data

[63] Continuation-in-part of Ser. No. 900,840, Jun. 18, 1992, abandoned.

[30] Foreign Application Priority Data

Jun. 18, 1991 [JP] Japan .................. 3-145882

[51] Int. Cl.$^6$ ............................ A61M 21/00
[52] U.S. Cl. ............................ 600/27
[58] Field of Search ..................... 600/26–28

[56] References Cited

U.S. PATENT DOCUMENTS

| | | | |
|---|---|---|---|
| 4,315,502 | 2/1982 | Gorges | 128/1 C |
| 5,036,858 | 8/1991 | Carter et al. | 600/27 |
| 5,149,317 | 9/1992 | Robinson | 600/27 |

FOREIGN PATENT DOCUMENTS 3823402  1/1990  Germany .................. 600/27

OTHER PUBLICATIONS

Kouhei Harada, "Dynamic Performance of Alpha Waves When A Person Is Settled Down or Under An Exposure of Flash Lights", J. of Society of Electrical Engineers, vol. 108 No. 2.

Primary Examiner—Lee S. Cohen
Assistant Examiner—John P. Lacyk
Attorney, Agent, or Firm—Ratner & Prestia

[57] ABSTRACT

An illumination system comprises a 1st signal generator to generate signals with a frequency range of the alpha rhythms of human brain waves, a 2nd signal generator to generate signals with a power spectrum distribution expressed by $1/f^n$, where n is between 0 and 2, and also with a frequency range below 50 Hz, a driver amplifier a and a driver amplifier b, both serving as light controllers to control the illumination of light sources according to the signals from the 1st and 2nd signal generators respectively and finally a light source 1 and a light source 2 to shed lights, and contributes to inducing a person under the light shedding from it to generate alpha rhythms without having an uncomfortable impression due to flickering illumination in a readily available illumination environment. Thus, the illumination from the light source 1 contributes to the entrainment of alpha rhythms and that from the light source 2 contributes to masking the illumination from the light source 1 eliminating the unpleasant flickering impression with a resultant ready creation of an illumination environment wherein alpha rhythms are induced. If necessary, it is possible to enhance the alpha rhythm entrainment effect by using sounds and also it is possible to apply a biofeedback for stabilizing and intensifying the alpha rhythms through a brain wave feedback loop formed visually and/or acoustically, if necessary, with the analyzed signals of the brain waves from a person under the illumination environment used as the control signals for the 1st signal generator.

11 Claims, 2 Drawing Sheets

ILLUMINATION EQUIPMENT

This application is a continuation-in-part of application Ser. No. 07/900,840, filed Jun. 18, 1992, now abandoned.

BACKGROUND OF THE INVENTION

1. Field of the Invention

This invention relates to illumination equipment for inducing alpha rhythms in human brain waves.

2. Description of the Prior Art

It has been long known that many alpha rhythms are observed in brain waves under an exposure of 12 Hz intermittent flash lights. The alpha rhythms are usually observed in brain waves of a person when he is settling himself down with his eyes closed or relaxing and the stimuli from the flash lights trigger an entrainment of the alpha rhythms. This is described in "Dynamic Performance of Alpha Waves When A Person Is Settled Down or under An Exposure of Flash Lights" by Kouhei Harada et al., Vol. 108 No. 2, Journal of Society of Electrical Engineers which is herein incorporated by reference for its teachings in the field of alpha waves. However, it is said according to the experiences acquired in lighting that an unpleasant flickering impression occurs under the monotonous intermittent flash lighting at around this frequency of 12 Hz.

Also, as a method to induce a person to relaxation by an exposure to intermittent lighting, a goggle like apparatus equipped with a light source capable of emitting a high level of illumination has been in use. The goggle like apparatus is worn by the person in the same manner as a skiing goggle is worn and flash lights of a high illuminating power are shed on the closed eyes intermittently. This method is more fully described in "Learning Relaxation Device" Gorges, D. E. U.S. Pat. No. 4,315,502.

However, a goggle like apparatus is required and the eyes are desirably closed when this method is employed. Further, such performance problems as fluctuations in intermittent flashing, etc. are not even hinted at all in this document.

SUMMARY OF THE INVENTION

This invention provides illumination equipment whereby alpha rhythms are induced in a person with his eyes kept open without resorting to a monotonous intermittent stimulation from flashing lights that causes an unpleasant impression of flickering and without using a specially-made equipment that makes it difficult to readily realize the required lighting conditions.

The illumination equipment of an exemplary embodiment of this invention has a 1st signal generator whereby signals of a frequency ranging from 8 Hz to 13 Hz are generated, a 2nd signal generator whereby signals with a power spectrum distribution of $1/f^n$, where n is between 0 and 2, and also with a frequency range not exceeding 50 Hz and a light controller whereby the illumination equipment is controlled according to the signals from the 1st and 2nd signal generators.

Also, the 1st signal generator has a signal synthesizer whereby the generated signals are made to fluctuate over the frequency range of 8 Hz to 13 Hz.

Besides, the 2nd signal generator has a signal synthesizer whereby the n of the power spectrum distribution $1/f^n$ is made variable.

Further, the illumination equipment has a multiple number of light sources and each of the 1st and the 2nd signal generators has its own lighting controller. Thus, each light source is operated independently.

Furthermore, the illumination equipment has the 1st signal generator and also a provision for an audio input function whereby the 2nd signal generator is replaced in running the lighting controllers that control the light sources.

In addition, an amplifier to amplify the signals gained through an audio signal input function and also a speaker to convert the audio signals to an acoustic energy so that the inputted audio signals can be monitored by listening.

Moreover, the illumination equipment has a light output controller whereby the light output level of the light sources that are controlled according to the signals from the 1st and the 2nd signal generators is adjusted freely in the maximum and the minimum values of its variation and also has a light output controller whereby a ratio of the light output level that is controlled by the 1st signal generator to the one that is controlled by the 2nd signal generator is made adjustable.

Also, a brain wave measurement instrument and a brain wave analyzer are made available for measurement and analysis of the brain waves of a person who is placed in the illumination environment provided by the illumination equipment of this invention and the analyzed brain waves are inputted to the 1st signal generator as the control signals.

Additionally, a converter to convert the signals from the 1st signal generator to audible rhythms and an amplifier to amplify the converted signals and also a speaker to convert the amplified signals electro-acoustically are made available.

Thus, light is generated at a frequency ranging from 8 Hz to 13 Hz and with a power spectrum distribution of $1/f^n$, where n is between 0 and 2, for the frequency range below 50 Hz. Under this condition wherein the light generating is taking place at a frequency of 8 Hz to 13 Hz, inducement and entrainments of alpha rhythms are brought about. Also, a masking effect whereby the light generating at the frequency of 8 Hz to 13 Hz is not felt bothersome is brought about for the light shedding of the power spectrum distribution of $1/f^n$, where n is between 0 and 2, for the frequency range below 50 Hz.

Although there is a certain variation from person to person, a human brain is entrained by a stimulation caused by the intermittently flashing lights of about 12 Hz and alpha rhythms are generated. Once this entrainment of alpha rhythms takes place, the entrainment of alpha rhythms is sustained even if the light generating frequency (functioning as a pace maker) may fluctuate. This is attributed to the hysteresis characteristics a human brain supposedly has from a nonlinear vibrating body.

When a fluctuation is deliberately applied to the light generating frequency according to the individual variance in the alpha rhythm entrainment frequency, it is possible to induce many people to generate alpha rhythms smoothly without much difficulty.

In addition, by separating the periodic light stimulus applied into a pace keeping function for the alpha rhythm entrainment and a masking function for not being bothered by the intermittent light shedding, it is possible for the operator of the equipment to have the balance between the two kinds of light stimulus and the generated light level arbitrarily adjusted and consequently to have the illumination environment most appropriately established to the individual differences in human sensory responses.

When the figure "n" to represent the level of light stimulus for masking is close to 0, the frequency of the light generating is increased to give a busy impression to the illumination environment and when the "n" is near 2, the light generating frequency is slowed down to provide a quiet impression.

By having the signal source for the light stimulus which has a power spectrum of $1/f^n$ and masks the light stimulus functioning as a pace maker for alpha rhythms replaced by audio signals, a light signal with an arbitrary number of "n" can be obtained from desirable music software without resorting to the use of a signal synthesizer having a complicated circuit constitution.

In addition, by having the music signals converted by a speaker to an acoustic output and then having the acoustic output being sensed by ears and the light output being sensed by eyes well matched with each other, a more stabilized impression of the test environment can be realized. Moreover, through the acoustic expression of the rhythms whereby generating lights keep pace with alpha rhythm inducement, the alpha rhythms are confirmed by ears.

At this time the maximum value and the minimum value of changes in the light output of the generating light sources can be adjusted arbitrarily and by making the ratio of the light output of the foregoing 1st signal generator to that of the 2nd signal generator changeable, it is possible for the operator of the illumination equipment of this invention to control the illumination to his taste of liking.

Furthermore, by having the alpha rhythms of a person who is exposed to the light generating from the illumination equipment of this invention measured and analyzed and having the analyzed brain waves used as the signals of the 1st signal generator, it is possible to feed back the alpha rhythms with a resultant enhanced contribution to the generation of alpha rhythms.

DESCRIPTION OF THE PREFERRED EMBODIMENTS

Figure 1:
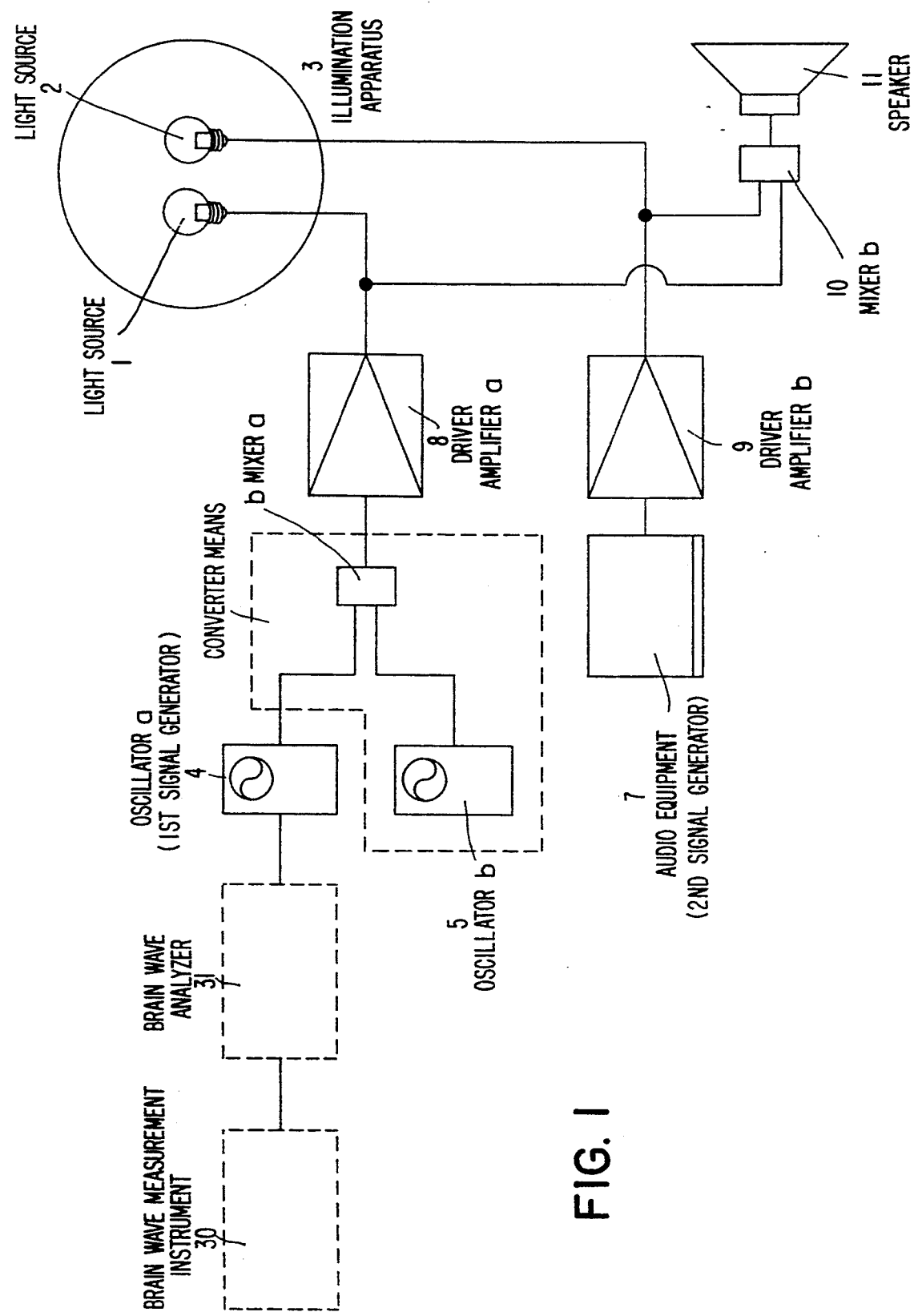
FIG. 1 is a schematic diagram to show the constitution of an example of the illumination equipment of this invention.

FIG. 1 illustrates schematically one example of the illumination equipment of this invention.

The illumination equipment is characterized by having a 1st signal generator whereby a signal with the frequency falling within a range of alpha rhythms is generated, a 2nd signal generator incorporated with a signal synthesizer whereby a signal having a power spectrum distribution of $1/f^n$, where n is between 0 and 2, and a frequency range of lower than 50 Hz is generated and a light controller whereby light generation from light sources is controlled according to the signals from the 1st and the 2nd signal generators.

Item 1 is a light source that illuminates at the frequency of alpha rhythms ranging from 8 to 13 Hz. Item 2 is a light source that illuminates at the frequency corresponding to f and not exceeding 50 Hz. In this case, the power spectrum distribution of the illumination is expressed by $1/f^n$ where n is between 0 and 2. Item 3 is an illumination apparatus comprising light sources 1 and 2. Item 4 is an oscillator a that generates a signal with the frequency corresponding to that of alpha rhythms ranging from 8 Hz to 13 Hz. Item 4 is a 1st signal generator. Item 5 is an oscillator b that generates an audio signal of 1.2 KHz serving as the carrier signal for the signals of the oscillator a. Item 6 is a mixer a that puts together the signals from the oscillators a and b and adjusts the mixing balance between both signals. The item 5, the oscillator 6, and the item 6, the mixer a, are grouped together and defined as a converter. Item 7 is an audio equipment serving as a 2nd signal generator that generates music signals with a power spectrum distribution of $1/f^n$, where n is between 0 and 2, according to the kinds of the reproduced music signals. Item 8 is a driver amplifier a that amplifies the output signal from the item 6, mixer a, and controls the light source 1. Item 8 may be characterized as a 1st light controller. Item 9 is a driver amplifier b that amplifies the signals from the audio equipment 7 and controls the light source 2. Item 9 may be characterized as a 2nd light controller. Item 10 is a mixer b that mixes the signals from the driver amplifier a, item 8, and the driver amplifier b, item 9, and adjusts the mixing balance between the two signals. Item 11 is a speaker that converts the signals from the mixer b, item 10, to sounds.

The 1.2 KHz audio signal generated by the oscillator b, item 5, is fed to the mixer a, item 6, as a carrier and modulated by the alpha rhythm frequency ranging from 8 Hz to 13 Hz. The signal modified by the mixer a, item 6, is inputted to the driver amplifier a, item 8, and the output from the driver amplifier a, item 8, controls the illumination of the light source 1. When the carrier signal of the 1.2 KHz audio signal is converted to lights by the light source 1, the lights emitted look continuous without any flickering due to the time-frequency characteristics of human vision since the flickering frequency is so high as to exceed the recognition limit of the human visionary capability. Therefore, only the light fluctuation with the alpha rhythm frequency ranging from 8 Hz to 13 Hz is recognized by human eyes as the output from the light source 1.

The output of the driver amplifier a, item 8, is mixed with that of the driver amplifier b, item 9, by the mixer b, item 10, and then acoustically converted by the speaker 11. Since the frequency of 8 Hz to 13 Hz is below the audible limit of human ears, the output from the speaker 11 is a sound of 1.2 KHz with a strong and weak rhythm ranging from 8 Hz to 13 Hz. By having a volume control incorporated with the mixer the sound strength can be controlled arbitrarily.

With the present example the constitution of the system is made simpler than the one using an exclusive signal generator by using the audio equipment 7 for an arbitrary supply of audio music signals as the signal synthesizer that generates signals with a power spectrum distribution of $1/f^n$, where n is between 0 and 2, and also with the principal wave length band of the power spectrum distribution ranging below 50 Hz. The audio signals outputted by the audio equipment 7 are amplified by the driver amplifier b, item 9, and converted to lights by the light source 2. At this time it is not necessary to cut off the high frequency element of the audio signals by using a high-cut filter that passes the low frequency element since only the frequencies below 50 Hz are recognizable as a bright and dark flickering and the frequencies higher than that are not recognizable due to the time frequency characteristics of human eyes.

In this case there is no light output controlling function in particular that controls the ratio of the light output due to the 1st signal generator to that due to the 2nd signal generator. However, the same control of the light output ratio can be achieved by controlling the ratio between the gain of the driver amplifier a, item 8, and that of the driver amplifier b, item 9.

With the illumination equipment having a multiple number of light source, the circuit constitution can be made simpler by having the light stimulus for alpha rhythm pace making and that for masking performed by two separate light sources and consequently resulting in no necessity of illumination of the light sources performed through the process of mixing of the signals from the 1st and the 2nd signal generators.

Also, by having the signals from the 1st and the 2nd signal generators expanded or compressed through a log amplifier before the signals are inputted in the driver amplifiers a, item 8, and b, item 9, respectively and also by having the minimum light output values established with no signals from the 1st and 2nd signal generators inputted to the driver amplifiers a, item 8, and b, item 9, the maximum and the minimum values of the fluctuation in the light output of the light sources 1 and 2 can be set up arbitrarily.

Here, the effect of alpha rhythm entrainment as achieved by the illumination equipment of an exemplary embodiment of this invention is examined.

The illumination equipment of an exemplary embodiment of this invention generates lights at a frequency ranging from 8 Hz to 13 Hz and with a power spectrum distribution of $1/f^n$, where n is between 0 and 2, for the frequency range below 50 Hz. At this time the light generated with a frequency of 8 Hz to 13 Hz brings about an alpha rhythm entrainment and the light generated with a power spectrum distribution of $1/f^n$, where n is between 0 and 2, for the frequency range of less than 50 Hz shows the effect of masking which prevents shedding lights at a frequency of 8 Hz to 13 Hz from causing any bothersome stimuli.

The frequency band of alpha rhythms falls in the frequency range of 8 Hz to 13 Hz and the lights illuminating within this frequency band are serving as a pace maker in entraining alpha rhythms. Although there is some variation from person to person, the alpha rhythm entrainment occurs generally at around 12 Hz.

Further, the effect of providing a fluctuation to the light generating that is taking place in the frequency range of 8 Hz to 13 Hz with the illumination equipment of an exemplary embodiment of this invention is examined here.

Once an alpha rhythm entrainment starts, that state is sustained in the brain even if the light generation acting as a pace maker fluctuates in its frequency since the alpha rhythms of a human brain that is considered as a non-linear vibrating body, has hysteresis characteristics. This is described by Kazuo Nakazawa, et al.: "Non-linearity of Vibrating Body That Generates Alpha Rhythms" Medical Electronics & Bio-Technology Vol. 23 No. 1. In other words, a deliberate application of fluctuations to the frequency at which light shedding as a pace maker for alpha rhythm generation is taking place as in this invention makes it possible for many people, whose alpha entrainment frequencies differ from person to person, to be induced to a smooth generation of alpha rhythms.

One example of the light sources that have fluctuations for the alpha rhythm inducing frequency band within their flickering frequency band is a flame. It has a power spectrum distribution of $1/f^n$, where n is between 0 and 2, for a wide range of frequency beyond the scope of 8 Hz to 13 Hz. By masking the light generation having frequencies that act as alpha rhythm pace makers by such a light of a wide frequency band as a flame, an image of flame flickering is provided to eliminate a rather monotonous light stimulus for the frequency range of 8 Hz to 13 Hz and also to soften an unpleasant impression of fluctuations.

By having the function of the periodic light stimulus separated into one function that acts as pace making for alpha rhythm generation and another function that serves as masking, it is possible to create at will an illumination environment where individual differences in sensing are well taken into consideration.

In addition, when the n of fluctuations in the light stimulus for masking is near 0, the light generating frequency of the illumination equipment increases and provides a noisy impression. When the n is close to 2, the light generating frequency slows down and gives a quiet impression.

At this stage, the effect of an increased acoustic feedback is examined.

Figure 2:
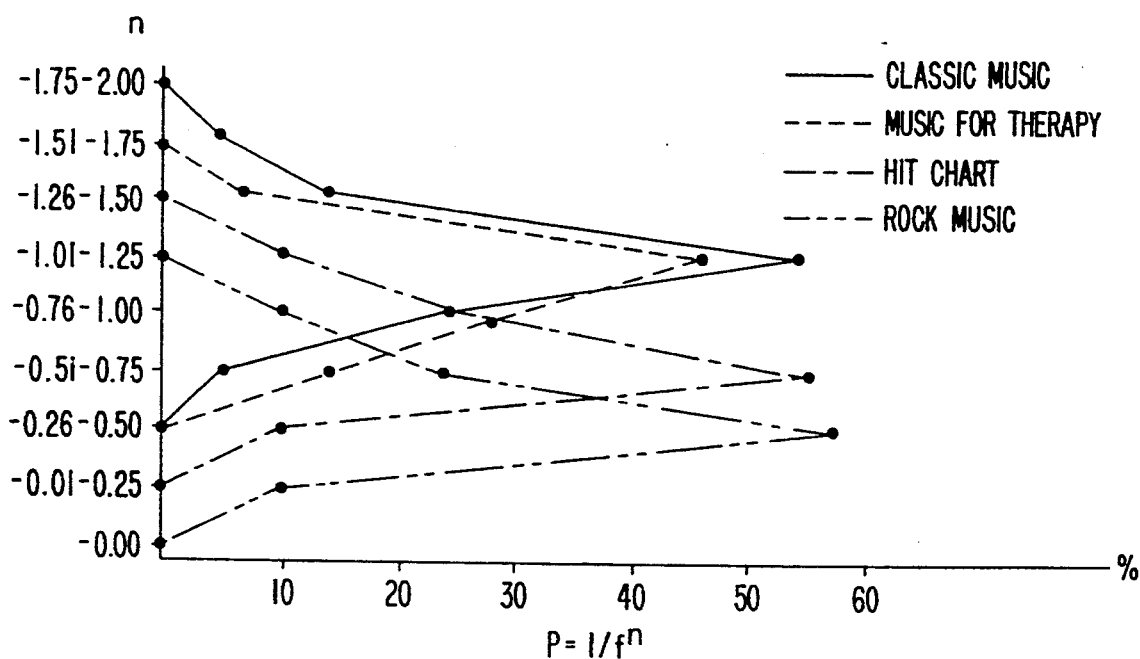
FIG. 2 is a demographic drawing to show the relationship between the types of music and the spread of "n".

By having the signal source for the light stimuli that possess characteristics of $1/f^n$ power spectrum distribution and mask the light stimuli functioning as a pace maker for alpha rhythm generation replaced by an audio signal source, the light signals of the "n"th degree distribution are obtained from desirable music softwares without relying on a signal synthesizer of complicated circuits. For a reference the general relationship between the kinds of music and the spread of "n" is shown in FIG. 2. This is explained in "1991 Amenity Market and Future Perspective", P 371-P 374 of Study Group of Japan Bio-Music, Compiled by Fuji Economy Co., Ltd., Osaka Bureau, Amenity Project Preparatory Office which is herein incorporated by reference for its teachings in the field of music.

In addition, by having the music signal converted acoustically through a speaker, the illumination changes sensed by eyes and the sound changes sensed by ears are matched with each other, resulting in the generation of the more stable images. Besides, by having the rhythm of the light stimulus to work as a pace maker for alpha rhythms tuned with sounds, the alpha rhythms are made recognizable by ears.

At this time, the maximum and the minimum values of the variation in the lights outputted from the light source can be set up arbitrarily and by having the ratio of the light output derived from the first signal generator to that from the second signal generator made variable, the illumination changes of the illumination equipment of this invention can be adjusted to the liking of the operators.

Figure 3:
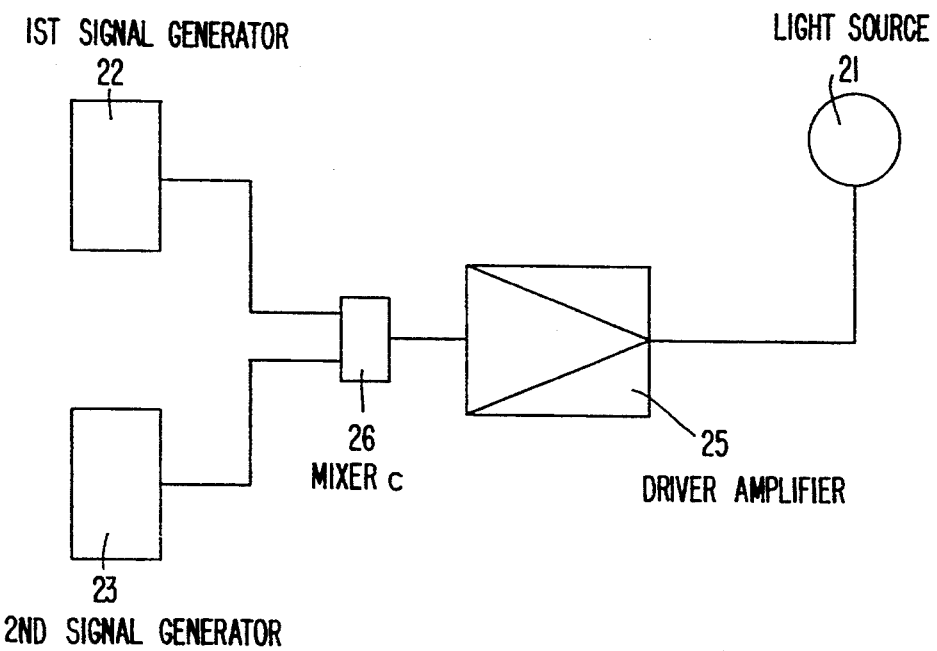
Fig. 3 is a schematic diagram to show the constitution of another example of the illumination equipment of this invention.

Another exemplary embodiment of the present invention is illustrated by FIG. 3. As shown in this Figure, it is possible to combine the driver amplifier item 25 and the light source item 21. Mixer C 26 is mixing the signals from the 1st signal generator item 22 and the 2nd signal generator 23 before the signals are inputted to the driver amplifier. In this example, though, the circuit constitution is made simpler by having a multiple number of light sources with each light source illuminated by a separate light controller, respectively, like FIG. 1, that as incorporated with either the 1st or the 2nd signal generator. In this case, the mixer C 26 has a light output controlling function in particular that controls the ratio of the light output due to the 1st signal generator to that due to the 2nd signal generator. However, driver amplifier item 26 can control the ratio between the gain of the 1st signal generator, item 22, and that of the 2nd signal generator, item 23.

The brain wave analysis and the effect of its feedback to the individuals under test is next examined.

It is generally recognized as a bio-feedback to obtain stabilized and intensified alpha rhythms by having the alpha rhythms generated in a human brain expressed either in a visually recognizable form or in an audible way and fedback to the individual under test. This is described in QI L, ZUMOS ENG Z: "Investigation on visually evoked response driven by sine modulated light and alpha feedback rhythm", Proc. Annu. Conf. IEEE Eng. Med. Biol. Soc. 10th Vol. 3.

Therefore, by having a brain wave measurement instrument 30 and a brain wave analyzer 31 prepared in order to measure and analyze the brain waves of a person who is placed in the illumination environment provided by the illumination equipment of this invention and by having the analyzed brain waves used as the control signals for the 1st signal generator, a brain wave feedback loop formed through a vision sensing the generation of light and another brain wave feedback loop formed through an audio sensibility. Thus, the alpha rhythms generated in an individual are transformed to pieces of visually recognizable information as well as audible information and fedback to the individual under test with a resultant completion of the bio-feedback that stabilizes and intensifies the alpha rhythm generation.

Thus, a supply of an illumination equipment whereby an illumination environment is readily established to entrain alpha rhythms without giving an unpleasant flickering impression and without necessitating the eyes to be closed is realized by this invention. Also, if necessary, its effectiveness can be enhanced by the additional use of an audio feedback.

A subjective evaluation carried out by several tens of persons with the illumination equipment of this invention has revealed that more than half of the persons had good impressions such as "gaining flame like fluctuation images" and comfortable mood creating illumination. Further, it is made readily possible that the images created by illumination are changed according to the accompanying music for the better illumination effect.

What is claimed is:

1. An illumination control system comprising:
   a first and second light source;
   a first signal generator wherein a first signal with a frequency ranging from 8 Hz to 13 Hz is generated;
   a second signal generator wherein a second signal with a power spectrum distribution expressed by $1/f^n$, where n is between 0 and 2 and with a frequency ranging below 50 Hz is generated; and
   a first light controller controlled by said first signal generator, said first light controller driving said first light source;
   a second light controller controlled by said second signal generator, said second light controller driving said second light source;
   wherein light generation from said first light source is controlled by said first signal from said first signal generator and light generation from said second light source is controlled by said second signal from said second signal generator.

2. An illumination control system comprising:
   light source;
   a first signal generator wherein a first signal with a frequency ranging from 8 Hz to 13 Hz is generated;
   a second signal generator wherein a second signal with a power spectrum distribution expressed by $1/f^n$ where n is between 0 and 2, and with a frequency ranging below 50 Hz is generated; and
   a light output controller coupled between said first signal generator and second signal generator
   for controlling said first generator and said second generator and connected to said light source for driving said light sources;
   wherein light generation from said light sources is controlled by signals from said first signal generator and said second signal generator.

3. An illumination control system as in claim 2 said light output controller further including a first light output controller to arbitrarily set the minimum value of the variation in light output from the first light source and the second light source illuminated by the first signal and the second signal from the first and the second signal generators respectively and a second light output controller to vary the ratio of the light output value controlled by the first signal generator to the light output value controlled by the second signal generator.

4. An illumination control system as in claim 2 said light output controller further including a second light output controller to arbitrarily set the maximum and the minimum values of the variation in light output from the light sources illuminated by the first signal and the second signal from the first signal generator and the second signal generator respectively.

5. An illumination control system according to one of claims 1, 3 and 2 wherein said first signal generator is equipped with a signal synthesizer having an oscillation frequency changing and fluctuating over a frequency range of 8 Hz to 13 Hz.

6. An illumination control system according to claim 5 further including a signal synthesizer connected to said second signal generator wherein the n in the power spectrum distribution, $1/f^n$, of said second signal generator is made variable and the value of n is arbitrarily set.

7. An illumination control system according to one of claims 1, 8 and 11 further including a signal synthesizer connected to said second signal generator wherein the n in the power spectrum distribution, $1/f^n$, of said second signal generator is made variable and the value of n is arbitrarily set.

8. An illumination control system according to one of claims 1, 3 and 2 wherein the second signal generator includes means for generating a audio signal input.

9. An illumination control system according to claim 8 further including an amplifier, connected to said means for generating an audio output signal, to amplify the audio signal input and a speaker, connected to said amplifier to convert the amplified signals acoustically.

10. An illumination control system as in one of claims 1, 3 and 2 further including a brain wave measurement instrument and a brain wave analyzer, connected to said first signal generator, to measure and analyze the brain waves of a person placed in an illumination environment created by said illumination equipment and to use the analyzed brain waves as control signals to the first signal generator.

11. An illumination control system as in one of claims 1, 3 and 2 further including a converter connected to said first signal generator, to convert signals from the first signal generator to audible rhythmic signals, an amplifier, connected to said converter to amplify the audible rhythmic signals and a speaker, connected to said amplifier, to convert the amplified signals acoustically.

* * * * *